United States Patent [19]

Giacobbe et al.

[11] Patent Number: 4,629,903
[45] Date of Patent: Dec. 16, 1986

[54] METHOD OF MONITORING A CATALYST FEED AND APPARATUS FOR IMPLEMENTING THE METHOD

[75] Inventors: Thomas J. Giacobbe, Skillman; Richard H. Leitman, East Brunswich; Walter Terebecky, Sayerville, all of N.J.

[73] Assignee: Mobil Oil Corporation, New York, N.Y.

[21] Appl. No.: 658,967

[22] Filed: Oct. 9, 1984

[51] Int. Cl.[4] .................. G01N 15/06; G01N 15/07
[52] U.S. Cl. .................................. 250/573; 250/227
[58] Field of Search .............. 250/573, 574, 575, 227; 356/436, 439

[56] References Cited

U.S. PATENT DOCUMENTS

| | | |
|---|---|---|
| 1,849,881 | 3/1932 | Pearson . |
| 3,036,153 | 5/1962 | Day .................................. 178/7.1 |
| 3,255,357 | 6/1966 | Kapany et al. ........................ 250/227 |
| 3,317,738 | 5/1967 | Piepenbrink et al. ................ 250/227 |
| 3,358,148 | 12/1967 | Conklin et al. ..................... 356/436 |
| 3,718,758 | 2/1973 | Ponghis et al. ...................... 178/6.8 |
| 3,864,044 | 2/1975 | Lyshkow ............................. 250/573 |
| 4,021,120 | 5/1977 | Muller et al. ....................... 250/573 |
| 4,260,258 | 4/1981 | Rose et al. .......................... 250/573 |

FOREIGN PATENT DOCUMENTS 2133797  1/1973  Fed. Rep. of Germany ...... 356/436

Primary Examiner—David C. Nelms
Assistant Examiner—William L. Oen
Attorney, Agent, or Firm—Alexander J. McKillop; Michael G. Gilman; Charles J. Speciale

[57] ABSTRACT

A method for monitoring the feed of a catalyst, especially the feed of a catalyst employed in a gas-phase linear low density polyethylene process system through the intermediary of the electro-optical scanning of an intermittent flow of the catalyst. The invention also relates to an apparatus for monitoring the catalyst feed in a gas-phase linear low density polyethylene process for the implementing of the inventive monitoring method. An intermittent flow of the catalyst, which is generally opaque, is monitored through the utilization of fiber optics and a light source and light detector device, wherein light which is conducted through the fiber optics passes through a clear or transparent flow channel through which there is effected the catalyst flow, and is monitored through a suitable photocell. The catalyst particles will interrupt the light beam while traversing the transparent flow channel and allow this to be registered by the photocell on a suitable indicating instrument.

6 Claims, 1 Drawing Figure

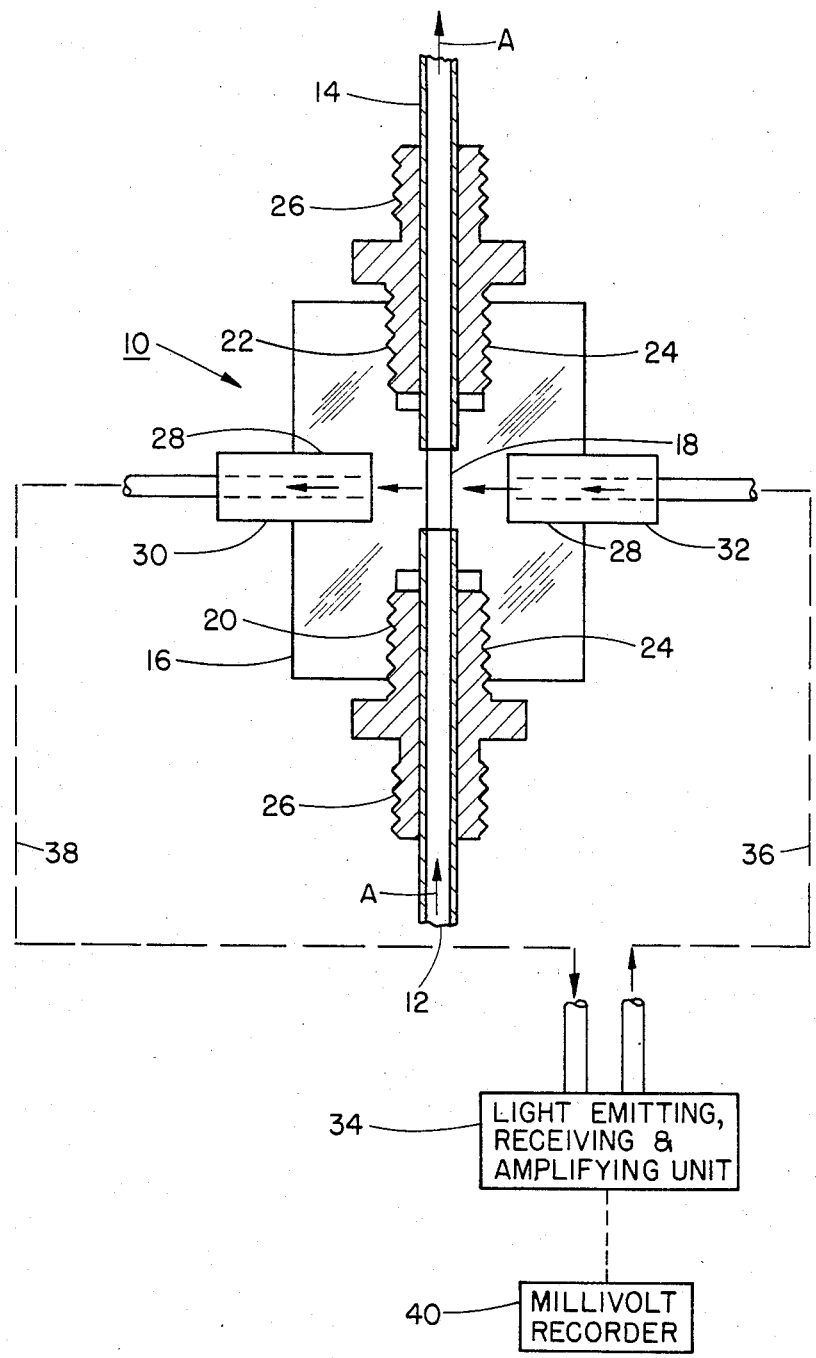

METHOD OF MONITORING A CATALYST FEED AND APPARATUS FOR IMPLEMENTING THE METHOD

BACKGROUND OF THE INVENTION

1. Field of the Invention

The present invention relates to a method for monitoring the feed of a catalyst, especially the feed of a catalyst employed in a gas-phase linear low density polyethylene process system through the intermediary of the electro-optical scanning of an intermittent flow of the catalyst. Furthermore, the invention relates to an apparatus for monitoring the catalyst feed in a gas-phase linear low density polyethylene process for the implementing of the inventive monitoring method.

Quite frequently, catalyst feed systems which are employed in gas-phase linear low density polyethylene processes and systems evidence a tendency to plug as to inhibit catalyst flow, or may, at times, fail to uniformly convey catalyst to the reactor which is utilized in the process. Such disruptions or undesirable fluctuations in the catalyst feed often necessitate the passage of hours of process reaction time before the poor feed conditions in the catalyst feed systems become evident in the LLDPE process; for instance, as may be indicated by a reduced reaction rate of the process. The problem is particularly troublesome during start-ups of the process system and reactor apparatus, at which point in time it is extremely difficult to precisely diagnose the cause of the reduced reaction rate of the process, inasmuch as numerous other causes can adversely affect or even completely inhibit initiation of the desired process reaction. Consequently, in order to enhance the economics and operating efficiency of such a process in determining the appropriate catalyst feed conditions for a gas phase LLDPE process system or reactor, it is of particular advantage to be able to incorporate a monitoring method and apparatus in the process which, almost instantaneously, will provide appropriate and rapid information as to whether the catalyst flow and feed into the LLDPE process system is being implemented at an appropriate feed rate and timing.

In order to achieve the foregoing, the present invention contemplates the utilization of a method and apparatus for monitoring the catalyst feed in a gas-phase linear low density polyethylene process, in which an intermittent flow of the catalyst, which is generally opaque, is monitored through the utilization of fiber optics and a light source and light detector device, wherein light which is conducted through the fiber optics passes through a clear or transparent flow channel through which there is effected the catalyst flow, and is monitored through a suitable photocell. The catalyst particles will interrupt the light beam while traversing the transparent flow channel and allow this to be registered by the photocell on a suitable indicating instrument.

2. Discussion of the Prior Art

Although numerous devices are presently known in the technology which employ methods for the electro-optical scanning of various materials, none of these devices and methods are directly applicable to the inventive method of monitoring the feed or flow of a generally opaque catalyst utilized in a gas-phase linear low density polyethylene process.

Kapany, et al. U.S. Pat. No. 3,255,357 discloses an arrangement for scanning imprinted graphical information on a continuously moving transparent tape by the projection therethrough of light through the intermediary of light-conducting optical fibers. The changes in the intensity of the light transmitted by the optical fibers upon passage through the continuously moving tape provides information over data imprinted on the transparent tape.

Pearson U.S. Pat. No. 1,849,881 discloses an apparatus for transmitting a beam of light through a continuously moving web of a substantially translucent material, such as paper, cloth or film, or liquids retained between generally flat glass plates or walls, and is employed to measure the light transmitting properties thereof. In this instance, the apparatus and method disclosed by Pearson is not readily applicable to a catalyst feed monitoring system in a gas-phase linear low density polyethylene process in which the catalyst is fed through a transparent flow secgtion in intermittent slugs or charges past the electro-optical or fiber optics scanning arrangement.

Ponghis, et al. U.S. Pat. No. 3,718,758 relates to an optical arrangement and method for monitoring the operation of a furnace, such as a blast furnace, in which a light conductor provides for the visual examination of the furnace charge, and of the walls and accessories of the furnace. This arrangement also is clearly inapplicable to the measurement and monitoring of an intermittent feed of a generally opaque catalyst in a gas-phase linear low density polyethylene process system.

Piepenbrink, et al. U.S. Pat. No. 3,317,738 discloses a photoelectric scanning arrangement in which a light conducting rod with a fluorescent portion is adapted to reflect light through the wall of a flow conduit in order to provide information with regard to the degree of opaqueness of a fluid which is conveyed through the conduit, and with regard to a material web adjacent a roller structure. This will enable an optical inspection to be effected for the presence of any holes, perforations or texture flaws in webs, contributed, for example of paper, metal foil, leather and the like. In this case, as in the other prior art discussed hereinabove, none of the scanning or monitoring methods and arrangements are adapted to provide for an electro-optical indication and information relative to the intermittent feed of a generally opaque catalyst employed in a gas-phase linear low density polyethylene process system.

Finally, Day U.S. Pat. No. 3,036,153 discloses an electro-optical scanning system for testing the opaqueness of various objects through the intermediary of light-transmitting optic fibers, wherein any variations in the degree of opaqueness or translucency are transmitted to a suitable receiver for information and evaluation. Also, in this instance is there no particular application of such a system to the monitoring of intermittent of feed catalyst charges utilized in the gas-phase of a linear low density polyethylene process system.

SUMMARY OF THE INVENTION

Accordingly, the present invention relates to a method and apparatus for monitoring the catalyst feed in a gas-phase linear low density polyethylene process system, in which intermittent slugs or charges of a generally opaque catalyst, which is employed in the LLDPE process system, are conducted through a flow conduit incorporating a transparent flow section, wherein light supplied from a light source is transmitted through optic fibers across the transparent flow section.

A device for detecting the presence of the flow of catalyst through the transparent flow section responsive to interruption of the light transmitted by the optic fibers and which is caused by the generally opaque properties of the catalyst, transmits this information for evaluation of the catalyst flow and feed conditions in the LLDPE process. Through the employment of the novel method and apparatus of the type described herein, it is possible to monitor the feed of the catalyst in a process system of a reactor for linear low density polyethylene, which is thus indicative as to whether the catalyst is being supplied in appropriate quantities for its use in the reactor system.

Accordingly, it is a primary object of the present invention to provide a method for monitoring the feed of a generally opaque catalyst employed in a gas-phase linear low density polyethylene process system.

It is a more specific object of the present invention to provide a method of the type described in which an intermittent flow of the catalyst is monitored through electro-optical scanning of the catalyst as the catalyst is conducted through the generally transparent flow section of a flow conduit.

Yet another object of the present invention is to provide a method of the type described in which the electro-optical scanning or monitoring of the intermittent flow of the catalyst is determined through the use of fiber optics transmitting a beam of light through the transparent flow section for the catalyst, and wherein the beam of light, after receiving the transparent flow section, is received by a suitable receiver device which will provide information over disruptions in the light transmitted through the transparent flow section indicative of a flow of the catalyst therethrough.

Yet another object of the present invention is to provide an apparatus for monitoring the feed of the catalyst in a gas-phase linear low density polyethylene process system implementing the inventive monitoring method.

BRIEF DESCRIPTION OF THE DRAWINGS

Reference may now be had to the following detailed description of an exemplary embodiment of an apparatus for monitoring the feed of a generally opaque catalyst in a gas-phase linear low density polyethylene process system by the electro-optical scanning of an intermittent flow of the catalyst through a transparent flow conduit, having reference to the single FIGURE of drawing schematically illustrating the apparatus.

DETAILED DESCRIPTION

Referring now in detail to the single FIGURE of drawing, the apparatus 10 for monitoring the intermittent feed or flow of a catalyst, which is employed in a gas-phase linear low density polyethylene process system, includes an inlet conduit 12, and an outlet conduit 14, preferably constituted of stainless steel tubing, wherein the inlet conduit 12 receives intermittent slugs or charges of a catalyst which is used in conveying nitrogen from a catalyst feeder to a reactor (not shown). The proximate ends of the conduits or tubes 12 and 14 communicate through the interposition of a transparent plastic block 16 which, for example, may be formed of a molded plastic material such as Lucite or the like. The block 16 includes a central through-passageway 18 forming a transparent flow section interconnecting the conduits 12 and 14.

Enlarged recesses 20 and 22 formed in the opposite ends of the block 16 which receive the respective ends of the conduits 12 and 14 internally of the block 16 are provided with internal screw threads 24 adapted to be engaged by complementary externally-threaded swagelock fittings 26 for clamping, in a fluid-tight sealing manner, both conduits 12 and 14 in the transparent block 16 in line with passageway 18.

Extending into transparent block 16 transversely across the direction of the flow passageway 18 are coaxially positioned recesses 28 in the block which, respectively, receive the end couplings 30, 32 for fiber optic cables or strands.

A suitable moduler light-emitting, receiving and amplifying unit 34 includes a light-transmitting fiber optic cable 36 which is connected to a suitable light source in the unit (not shown), and has one cable end communicating with the coupling 32 for orienting the end of the fiber optic cable 36 towards (and substantially normal to) the transparent flow passageway 18 in the block 16. Similarly, a fiber optic cable 38 having one end in the coupling 30 oriented in axial alignment with the proximate end of the fiber optic cable 36 extends to the light emitting, receiving and amplifying unit 34 so as to thereby form a completely operative circuit.

A millivolt recorder 40 is connected to the unit 34 and is adapted to receive and display information concerning the flow of catalyst through the transparent flow section 18 in the transparent block 16.

The operation of the inventive catalyst feed monitoring apparatus 10 is substantially as follows:

Under conditions in which no flow of catalyst take place through the conduits 12 and 14 and the intervening transparent flow passageway 18, any light conducted from the end of the fiber optic cable 36 towards the passageway 18 in the block 16 will pass through the block and be received without any disruption by the facing end of the fiber optic cable 38 in an axial alignment therewith, and then conducted to the light emitting, receiving and amplifying unit 34 and from there to the multivolt recorder 40 so as to provide indication that no catalyst is presently being conducted through in the conduits 12, 14, and 18; in effect, no catalyst is being introduced into the LLDPE process system at this time. Upon catalyst being conveyed from the catalyst feeder during the conveyance of nitrogen, a charge or slug of the catalyst, which is generally opaque, is conveyed from the process system, in the direction of arrow A through the conduit 12, the transparent flow passageway 18, and upwardly through the conduit 14 towards the reactor. During the flow or passage of any catalyst through the transparent flow passageway 18, the amount of light conveyed from the fiber optic cable 36 to the fiber optic cable 38 is substantially blocked from passing through the transparent passageway 18, and the unit 34 will supply information to the millivolt recorder to that, in effect, catalyst is flowing through the block 16 and, as a result, into the LLDPE process system.

From the foregoing, it becomes readily apparent that the present method and apparatus provides simple and efficient means of affording an accurate and instantaneous indication of the presence of a flow of catalyst through a reactor process system.

While there has been shown and described what are considered to be preferred embodiments of the invention, it will of course be understood that various modifications and changes in form or detail could readily be made without departing from the spirit of the invention. It is therefore intended that the invention be not limited to the exact form and detail herein shown and described, nor to anything less than the whole of the invention herein disclosed as hereinafter claimed.

What is claimed is:

1. An apparatus for continuously moinitoring the feed of a substantially opaque catalyst employed in a gas-phase linear low density polyethylene process system through the electro-optical scanning of an intermittent flow of the catalyst; comprising:
   (a) conduit means having an intermittent flow of said catalyst from said process system conveyed therethough, said conduit means including a generally transparent flow section having catalyst inlet and outlet flow means communicating with said system;
   (b) electro-optical means for scanning the passage of said catalyst through said transparent conduit flow section, said electro-optical means including:
      (i) at least one light-transmitting means for transmitting a light beam through said transparent flow section in a direction generally transverse to the flow of said catalyst through said flow section, said light-transmitting means comrprising light-conductive optic fibers; light-emitting means continually emitting light being connected to one end of one of said optic fibers for generating said light beam, the other end of said optic fiber being oriented to face towards the transparent flow section;
      (ii) at least one light-receiving means for receiving the light transmitted through said transparent flow section from said light-transmitting means;
   (c) and means connected to said light-receiving means for registering disruptions in the light transmitted through said transparent flow section indicative of predetermined intermittent flows of said catalyst through said process system.

2. An apparatus as claimed in claim 1, wherein said light-receiving means comprises a photocell responsive to said light beam so as to generate an electrical signal at said registering means indicative of interruption in the light transmitted through said transparent flow section.

3. An apparatus as claimed in claim 1, wherein said transparent conduit flow section comprises a transparent plastic block, a flow passageway for said catalyst extending through said block, said passageway having internal screw threads formed at the opposite ends thereof for threadingly engaging complementary threaded lock fittings for attaching said catalyst inlet and outlet flow means.

4. A method of continuously monitoring the feed of a substantially opaque catalyst employed in a gas-phase linear low density polyethylene process system through the electro-optical scanning of an intermittent flow of the catalyst; comprising: conveying an intermittent flow of said catalyst from said process system through a conduit having a generally transparent flow section; continuously electro-optically scanning the passage of said catalyst through said transparent flow section, including continually transmitting a light beam through said transparent flow section in a direction generally transverse to the flow direction of said catalyst through said conduit; and transmitting the light conducted through said transparent flow section from said light-transmitting means to light-receiving means for registering disruptions in the light transmitted through said transparent flow section indicative of intermittent flows of said catalyst through said process system.

5. A method as claimed in claim 4, wherein said light-transmitting means comprises light-conducting optic fibers; connecting light-emitting means to one end of one of said optic fibers, and orienting the other end of said optic fiber to face towards the transparent flow section.

6. A method as claimed in claim 4, wherein said light-receiving means comprises a photocell responsive to said light beam for generating an electrical signal at said registering means indicative of interruption in the light transmitted through said transparent flow section.

* * * * *